United States Patent [19]

Pinchuk

[11] Patent Number: 4,960,410
[45] Date of Patent: Oct. 2, 1990

[54] FLEXIBLE TUBULAR MEMBER FOR CATHETER CONSTRUCTION

[75] Inventor: Leonard Pinchuk, Miami, Fla.

[73] Assignee: Cordis Corporation, Miami, Fla.

[21] Appl. No.: 332,503

[22] Filed: Mar. 31, 1989

[51] Int. Cl.⁵ .............................. A61N 25/10
[52] U.S. Cl. ........................ 604/96; 604/280; 606/194
[58] Field of Search .................. 604/96–103, 604/280, 282; 606/192, 194; 128/657, 658

[56] References Cited

U.S. PATENT DOCUMENTS

| | | |
|---|---|---|
| 4,195,637 | 4/1980 | Gruntzig et al. |
| 4,202,346 | 5/1980 | Granier. |
| 4,323,071 | 4/1982 | Simpson et al. |
| 4,362,150 | 12/1982 | Lombardi et al. |
| 4,385,635 | 5/1983 | Ruiz ............................ 604/280 |
| 4,597,755 | 7/1986 | Samson et al. |
| 4,787,399 | 11/1988 | Bonello et al. ................ 604/96 |
| 4,798,586 | 1/1989 | Stevens ........................ 604/96 |

*Primary Examiner*—Stephen C. Pellegrino
*Attorney, Agent, or Firm*—Watts, Hoffmann, Fisher & Heinke

[57] ABSTRACT

A catheter having a two-part tubular member that defines a passageway which extends completely through the catheter. One part of the tubular member is a relatively stiff tube having a reduced wall thickness at its distal end that is spirally cut to increase its flexibility. A more flexible sheath covers the reduced thickness, distal portion of the relatively stiff tube to insure that the tubular member can hold pressure. A preferred flexible sheath or tube is constructed using a biaxially oriented polymer such as nylon or polyethylene.

12 Claims, 2 Drawing Sheets

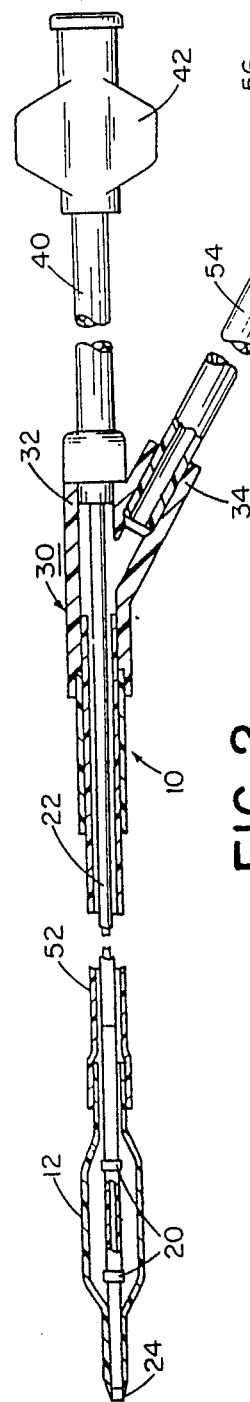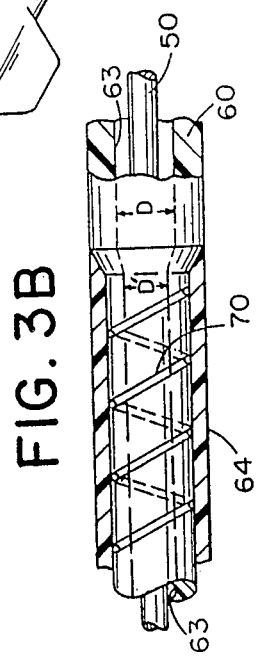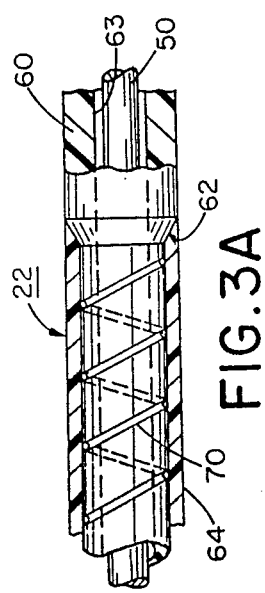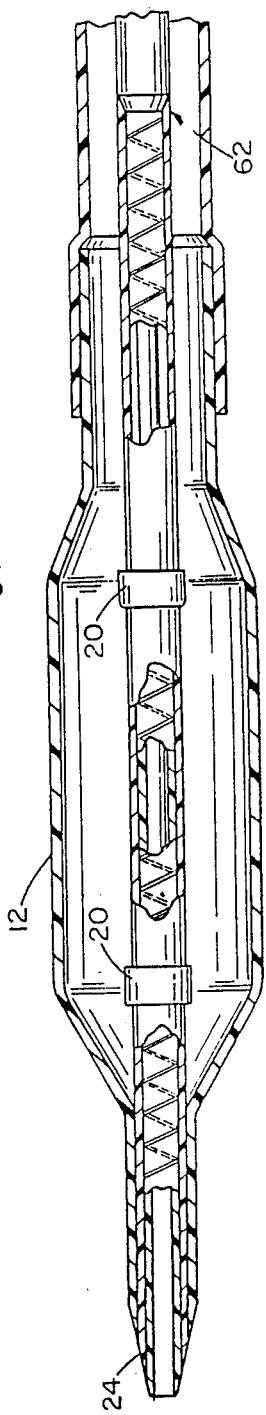
FIG. 2
FIG. 3A
FIG. 3B
FIG. 3

FLEXIBLE TUBULAR MEMBER FOR CATHETER CONSTRUCTION

Technical Field

The present invention concerns catheter construction particularly suited for use with an angioplasty catheter.

Background Art

It is known in the prior art to widen or open passageways within a subject with a balloon catheter. The balloon catheter's distal end is routed into the subject and guided along a path to a region of interest as the attending physician monitors progress of the catheter's distal end on a viewing screen. Once the catheter is properly positioned, the distally located balloon can be inflated to exert compression forces against passageway walls within the subject. One particular use of such a catheter is in opening partially or totally obstructed blood vessels in a subject.

U.S. Pat. No. 4,195,637 to Gruntzig et al. represents the state-of-the-art in balloon dilatation catheters in the late 1970's. The dilatation catheter disclosed in this patent had a cylindrical foldable wall which could be inflated to bring pressure to bear against a surface in close proximity to the balloon.

A later prior art patent concerning a flexible catheter tip is disclosed in U.S. Pat. No. 4,597,755 to Samson et al. which issued Jul. 1, 1986. In this patent, a catheter is disclosed having generally concentric inner and outer tubes that define passageways from the proximal to distal end of the catheter. The distal balloon forms an integral part of the outer tube. One aim of the '755 patent is to increase the flexibility of the central or inner member without sacrificing its ability to be pushed through a possibly tortious passageway to a region of interest without kinking. The mechanism for constructing such a catheter disclosed in the '755 patent includes a coil spring secured at a distal end of the inner or center tube. During construction of the catheter, a coil spring is mounted to a mandrel which is inserted into a suitably sized opening of the center tube. The flexible coil is left within the tube and a second piece of tubing placed over the spring and heat shrunk to make the flexible coil spring an integral part of the catheter's center tube. The catheter resulting from this construction has particular use in large bore applications such as heart, lung and renal catheters. Sharp bends can purportedly be traversed during the insertion process without kinking of the catheter.

U.S. Pat. No. 4,362,150 to Lombardi, Jr. et al. concerns a balloon catheter that has a two piece center tube. A distal end of the center tube has a flexible sleeve attached to a portion of the center tube that extends to the proximal end of the catheter. This construction makes the distal end of the center tube more flexible.

Disclosure of the Invention

The present invention concerns a catheter and most specifically concerns a flexible tubular member for such a catheter that facilitates catheter insertion. The catheter's tubular member has a first relatively stiff tubular portion which is made more flexible at one end by reducing its wall thickness and/or its diameter and in addition cutting a spiral groove along the reduced wall thickness or reduced diameter portion. This portion is covered with a flexible outer sheath or layer that allows the tubular member to hold pressure.

A tubular member so constructed allows a catheter to be inserted without kinking, yet is flexible enough to follow a winding path through a patient's cardiovascular system to a blocked region within a blood vessel and provides the pushability necessary to traverse a stenotic lesion. The resulting structure can be used to inject fluids into a subject and monitor blood pressure. These and other objects, advantages and features of the invention will become better understood from a detailed description of a preferred embodiment of the invention which is describe in conjunction with the accompanying drawings.

Brief Description of the Drawings

FIG. 2 is a partially sectioned view showing the balloon catheter in elevation;

FIG. 3 is an enlarged sectioned view of an extreme distal end of the balloon catheter showing a flexible innermember;

FIG. 3A is a further enlarged sectioned view showing a stepped-down region of the flexible innermember depicted in FIG. 3; and FIG. 3B is an enlarged section view showing an alternate stepped down region of the flexible innermember of FIG. 3.

Figure 1:
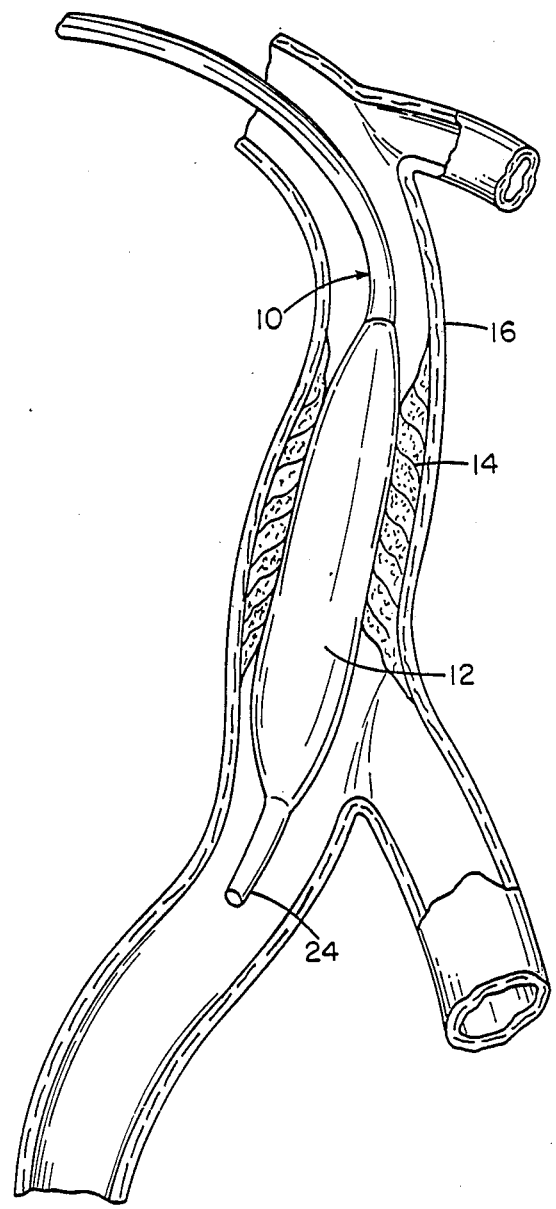
FIG. 1 schematically depicts a balloon catheter as it is being inflated to compress deposits within a blood vessel.

Best Mode for Carrying Out the Invention

Turning now to the drawings, FIG. 1 shows the distal end of a balloon catheter 10 having a distally located balloon 12. The balloon 12 is depicted in an inflated state to show its use in compressing deposits 14 that have partially blocked passage of blood through a blood vessel 16. The catheter 10 is routed to the vicinity of the deposits 14 by a physician who monitors progress of the catheter 10 as it is inserted through the patient's cardiovascular system. Techniques for inserting and routing balloon catheters to the vicinity of their intended use are known in the prior art.

To facilitate monitoring of the passage of the balloon 10 to the vicinity of the obstructions 14, two metallic bands 20 which are readily visible on a viewing screen are positioned within the balloon 12.

As seen most clearly in FIG. 2, the catheter 10 includes an inner tube 22 that supports the metal bands 20 and extends completely through the catheter 10 to the catheter's distal tip 24. At a proximal end of the catheter 10 (outside the patient) the catheter includes a relatively rigid bifurcating adapter 30 having an in-line branch 32 and side branch 34. The inner tube 22 extends into the in-line branch 32 and is connected to a hollow plastic tube 40 which extends from the in-line branch 32 of the adapter 30. Connected to the tube 40 is a leur fitting 42 which allows fluids (such as radiopaque dyes) to be injected into the catheter as well as allowing blood pressure to be monitored from the distal end of the catheter. In summary, the inner tube 22 provides a direct line of fluid communication from the distal end 24 directly through the catheter 10 to the leur fitting 42. In addition, a flexible guidewire, for example such as the guidewire 50 shown in FIGS. 3A and 3B, can be inserted into the leur fitting 42 and pushed completely through the catheter inner tube 22 to extend beyond the distal end 24 for help in positioning the catheter 10 during its insertion.

As seen most clearly in FIGS. 2 and 3, the catheter 10 also defines an outer tube 52 that extends from the adapter 30 along the length of the catheter to the balloon 12. The outer tube 52 defines an annular passageway that surrounds the inner tube 22 along its length and allows fluid to be injected into the catheter from the side branch 34 to inflate the balloon 12. A hollow plastic tube 54 engages the side branch 30 and is connected at its proximal end to a second leur fitting 56. By injecting an inflating fluid into the leur fitting 56 this fluid can be forced through the space between inner and outer tubes 22, 52 to fill the balloon 12, inflating it and bringing it into engagement with obstructions within a subject blood vessel.

As seen most clearly in FIGS. 3, 3A and 3B, the catheter's inner tube 22 includes a first rather stiff plastic tube 60 that extends from the bifurcating adapter 30 to the catheter's distal end 24. At a region 62 slightly proximal of the balloon 12 (FIG. 3), the tube 60 is machined (by centerless grinding) or alternately necked down by pulling the tube axially on a mandrel.

FIG. 3A depicts a tube 22 fabricated by centerless grinding of a distal portion of the stiff plastic tube 60. The tube has a reduced diameter but the center passageway 63 extending through the tube 60 is uniform along its length. The portion ground to the reduced diameter has a reduced wall thickness and is spirally scored or cut to increase its flexibility. This spirally cut portion of the tube 60 extends axially through the balloon to the catheter's distal end 24.

An alternate design (FIG. 3B) is fabricated by drawing the tube axially on a mandrel. The passageway 63 has a larger diameter D of approximately 0.025 inch along its proximal portion and a reduced diameter D' of 0.020 inch along the spirally cut portion. The wall thickness of the proximal portion of the tube 60 is approximately 0.005 inch so that an outer diameter of the tube is approximately 0.035 inch along the proximal portion. The wall thickness of the necked down portion is 0.003 inch so that the outer diameter of the tube's distal end is 0.026 inch for the alternate embodiment of FIG. 3B.

A second more flexible tube or sheath 64 covers and is bonded to the reduced diameter portion of the tube 60 from the start of the tube's reduced diameter to the catheter's distal end 24. The resulting composite inner member 22 has increased flexibility at the distal end over a tube having a uniform diameter and thickness along its entire length. This is advantageous since it allows the catheter to be inserted more easily along a tortious path through a subject's cardiovascular system without kinking and with improved pushability.

The spiral cut 70 (see FIG. 3A) can be made to extend partially through the wall of the reduced diameter tube 60 or alternately and preferably can extend completely through this wall. The angle the spiral cut 70 makes with respect to the center axis of the catheter can vary from 20° to 85°. A preferred spiral cut makes an angle of approximately 70° with respect to the center axis of the tube 60. The cut can be performed on a lathe having a razor blade secured to a tool post or alternately cut using a threaded die.

The stiff tube 60 can be constructed of materials having a shore hardness of 80A and greater. Materials suitable for this tube 60 are polycarbonate, polyacrylates, zytel 906, polyurethanes, polyesters, polyamide, Teflon, polyacetals, polyimides, polyphenolics, polyethylenes or metals such as stainless steel tubing.

The second more flexible tube 64 may be constructed using a more flexible material. Examples of these flexible materials include polyurethanes, soft nylons, silicone rubbers, natural rubbers, polyolefins, polyvinyl chlorides, polyethylenes or very thin versions of the stiffer materials used to construct the tube 60. The presently preferred flexible tube 64 is constructed from a biaxially oriented polymer such as nylon or polyethylene.

The tube 64 is attached to the tube 60 using adhesives. Alternatively the bonding can be accomplished by heat bonding, ultrasonic bonding, mechanical interlocks, heat shrinking, or the like. The tube 64 can also be formed about the tube 60 by dip coating the tube 60 into a suitable polymer containing solvent, by co-extrusion of the two tubes 60, 64 or by injection molding or the like.

The present invention has been described with a degree of particularity. It is the intent, however, that the invention include all modifications and/or alterations falling within the spirit or scope of the appended claims.

I claim:

1. A catheter for insertion into a subject comprising an elongated tubular member which extends from a proximal end to a distal end of said catheter and defines a passageway extending through said catheter from the proximal end to the distal end; said elongated tubular member including a first relatively stiff tube that is spirally cut along a distal portion to increase its flexibility and, includes an inner surface that defines said passageway and a second more flexible tube that covers the spirally cut distal portion of the stiff tube to make a distal portion of the elongated tubular member more flexible than a proximal portion of the elongated tubular member.

2. The catheter of claim 1 additionally comprising a second, outer tubular member and an inflatable balloon attached to an end of the outer tubular member, said balloon overlying a portion of said central elongated tubular member that includes the second more flexible tube and wherein a distal end of the balloon is bonded to the more flexible tube of said central elongated tubular member.

3. The catheter of claim 1 wherein a spiral cut extends completely through the thickness of said first relatively stiff tube.

4. The catheter of claim 1 wherein the portion of the first relatively stiff tube covered by the second more flexible tube has a reduced wall thickness and the passageway that extends through the catheter has a uniform diameter along its length.

5. The catheter of claim 1 wherein the spirally cut portion of the first relatively stiff tube covered by the second more flexible tube has a reduced diameter and the wall thickness is uniform, resulting in a reduced diameter passageway along said spirally cut portion of the stiff tube.

6. A catheter for insertion into a subject comprising a central elongated tubular member which extends from a proximal end to a distal end of said catheter and defines a passageway extending through said catheter from the proximal end to the distal end; said elongated tubular member including a first relatively stiff plastic tube having an inner surface that defines said passageway and a second more flexible plastic tube in engagement with a distal portion of the stiff plastic tube, said distal portion having a reduced wall thickness and a reduced outer diameter to make the distal portion of the stiff plastic tube more flexible, a second, outer tubular member, and an inflatable balloon attached to an end of the outer tubular member, said balloon overlying a portion of said central elongated tubular member including the second more flexible plastic tube and wherein a distal end of the balloon is bonded to the second more flexible plastic tube of said central elongated tubular member.

7. The catheter of claim 6 wherein the reduced wall thickness of the covered portion of the stiff plastic tube is cut in a spiralling cut.

8. The catheter of claim 7 wherein the spiralling cut extends completely through the reduced wall thickness of said first relatively stiff plastic tube.

9. A catheter for insertion into a subject comprising a central elongated tubular member which extends from a proximal end to a distal end of said catheter and defines a passageway extending through said catheter from the proximal end to the distal end; said elongated tubular member including a first relatively stiff plastic tube having an inner surface that defines said passageway and a second more flexible plastic tube in engagement with a distal portion of the stiff plastic tube, said distal portion having a reduced outer diameter to make said distal portion more flexible, a second, outer tubular member, and an inflatable balloon attached to an end of the outer tubular member, said balloon overlying a portion of said central elongated tubular member including the second more flexible plastic tube and wherein a distal end of the balloon is bonded to the more flexible plastic tube of said central elongated tubular member.

10. The catheter of claim 10 wherein a distal portion of the stiff plastic tube covered by the more flexible plastic tube is cut with a spiralling cut.

11. The catheter of claim 10 wherein the spiralling cut extends completely through the covered portion of said first relatively stiff plastic tube.

12. The catheter of claim 9 where the passageway through the relatively stiff plastic tube has a reduced diameter along a length of the covered portion of the relatively stiff plastic tube.

* * * * *